United States Patent
Seppanen et al.

(10) Patent No.: US 9,237,868 B2
(45) Date of Patent: Jan. 19, 2016

(54) FITNESS TEST

(75) Inventors: Mikko Seppanen, Rovaniemi (FI); Aki Pulkkinen, Tikkakoski (FI); Veli-Pekka Kurunmaki, Jyvaskyla (FI); Sami Saalasti, Jyvaskyla (FI); Joni Kettunen, Saynatsalo (FI)

(73) Assignee: Firstbeat Technologies OY, Jyväskylä (FI)

( * ) Notice: Subject to any disclaimer, the term of this patent is extended or adjusted under 35 U.S.C. 154(b) by 604 days.

(21) Appl. No.: 12/990,005

(22) PCT Filed: May 4, 2009

(86) PCT No.: PCT/FI2009/050351
§ 371 (c)(1), (2), (4) Date: Oct. 28, 2010

(87) PCT Pub. No.: WO2009/133248
PCT Pub. Date: May 11, 2009

(65) Prior Publication Data
US 2011/0040193 A1  Feb. 17, 2011

(30) Foreign Application Priority Data
May 2, 2008  (FI) ...................................... 20085402

(51) Int. Cl.
*A61B 5/02* (2006.01)
*A61B 5/22* (2006.01)
*A61B 5/11* (2006.01)

(52) U.S. Cl.
CPC ............... *A61B 5/222* (2013.01); *A61B 5/1118* (2013.01)

(58) Field of Classification Search
CPC ....................................................... A61B 5/222
USPC ............... 600/300, 301, 500, 502, 483–484, 600/508–509, 529; 482/8–9, 900–901
See application file for complete search history.

(56) References Cited

U.S. PATENT DOCUMENTS

| | | | | |
|---|---|---|---|---|
| 5,697,378 | A * | 12/1997 | Elghazzawi | 600/508 |
| 6,176,241 | B1 | 1/2001 | Blau et al. | |
| 6,512,948 | B1 | 1/2003 | Shiga et al. | |
| 6,687,535 | B2 * | 2/2004 | Hautala et al. | 600/520 |
| 7,310,549 | B1 * | 12/2007 | Angelini et al. | 600/509 |
| 7,822,472 | B1 * | 10/2010 | Xi | 600/519 |
| 2007/0197920 | A1 * | 8/2007 | Adams | 600/483 |
| 2007/0232454 | A1 * | 10/2007 | Kagan et al. | 482/8 |
| 2007/0299330 | A1 * | 12/2007 | Couronne et al. | 600/368 |
| 2008/0033311 | A1 * | 2/2008 | Sledge | 600/509 |
| 2008/0161653 | A1 | 7/2008 | Lin et al. | |
| 2008/0300498 | A1 * | 12/2008 | Edwards | 600/520 |
| 2010/0292598 | A1 * | 11/2010 | Roschk et al. | 600/519 |

FOREIGN PATENT DOCUMENTS

| | | |
|---|---|---|
| WO | 2004/016173 | 2/2004 |

* cited by examiner

*Primary Examiner* — Navin Natnithithadha
*Assistant Examiner* — Eric Messersmith
(74) *Attorney, Agent, or Firm* — Maier & Maier, PLLC

(57) ABSTRACT

This document describes a fitness test application which allows the user to exercise freely (running and cycling outdoors, bicycle ergometer, rowing ergometer, treadmill) and which provides an estimate of user's fitness during and/or after the exercise. The analysis can be performed either as real-time or as post-analysis.

8 Claims, 6 Drawing Sheets

FITNESS TEST

BACKGROUND OF THE INVENTION

1. Field of the Invention

This invention relates to a method and an assembly for assessing of person's cardiorespiratory fitness, which is one of the most significant nominators of human health and longevity.

2. Description of the Related Art

Prior art comprises many ways to assess fitness. Traditionally fitness tests are performed under the supervision of testing personnel. One option is to utilize direct measurement of respiratory gases during a maximal exercise test during which person's maximal oxygen uptake is determined from the analyzed respiratory gases. There are also a great number of methods to assess fitness indirectly under submaximal exercise but these tests as well as maximal exercise tests require testing personnel to conduct and supervise the test. Some of both maximal and submaximal tests can be performed also in field conditions thus not requiring exercise equipment.

Recently free fitness test modes have also been introduced in EP0709058 (Alessandri), U.S. Pat. No. 6,882,955 (Ohlenbusch & Darley), FR2867055 (Quilliet & Billat), US2007/0082789 (Nissila, Niva, Jaatinen & Kinnunen), and by Weyand et al. (2001)). These tests combine measurement of heart rate and speed during user performed exercise where the maximal oxygen uptake is determined e.g., using simple mathematical calculations. Speed can be measured by using accelerometry based measures, by using a satellite navigation system (e.g. global positioning system, GPS) or a local positioning system (e.g. using a WiFi network). Current state of art doesn't however know a method which would evaluate and segment measured data to form an accurate measure of cardiorespiratory fitness but rather only give a rough estimate of person's or animals daily performance. Current state-of-art doesn't either know solution where person's fitness information gathered during a freely performed exercise session, is used to guide a user to a physiological target state. Neither does current state-of-the-art know a method wherein the user's dynamically changing training plan is automatically updated based on his estimated fitness level.

Consequently, this invention introduces a system and method for accurate and sophisticated assessment of person's cardiorespiratory fitness during any user performed exercise session. Accurate assessment is performed by means of data segmentation and evaluation. Estimate of cardiorespiratory fitness can be also utilized in guiding the user during an exercise to reach a preset (set by the user or by an automatic) physiological target state wherein the fitness estimate may have been calculated in the beginning part of the same exercise. Estimate of cardiorespiratory fitness can be also utilized in creating a dynamically changing training plan for the user wherein training plan can be updated if person's fitness level has changed.

BRIEF DESCRIPTION OF INVENTION

The object of this invention is to achieve an improved method for estimating fitness, wherein a person exercises freely and his/her cardiorespiratory fitness is estimated based on recorded information. This object is achieved with the features described in accompanying claim 1. A system for implementing the method is achieved with the features in accompanying claim 9.

Estimate of person's fitness can be given based on one session only if the data is reliable but combination of several exercise sessions can be also used in estimation.

Selecting or weighting the data segments for determination of person's fitness in addition to data collection and statistical analysis only, is the unique feature of the described invention. Determination of person's cardiorespiratory fitness means determination of aerobic exercise capacity usually measured as VO2max or METmax (MET=Metabolic Equivalent, 1 MET=the level of person's resting metabolic rate). Determination of cardiorespiratory fitness can be also done by scaling measured VO2max or METmax based on person's age and gender which produces a fitness class. A preferred method comprises the following steps:

1) User selects exercise type and inputs his/her personal parameters (at least age, preferably maximal heart rate). Later on maximal heart rate can be determined during user-performed exercise sessions and updated if necessary.
2) Collection of heart beat data and performance data during user-performed exercise session(s). User can exercise freely but it is also possible to give the user broad recommendations on how to get most accurate results.
3) Segmenting collected data to different heart rate ranges
4) Calculating the reliability of different data segments
5) Calculating weighting coefficients for different data segments based on their reliability or excluding low reliability data segments from further analysis wherein low reliability is characterized by following factors:
   Data segments at the very beginning of every exercise session (e.g. first 3 minutes)
   Data segments with significant changes in heart beat derivable intensity parameters or in external workload
   If not measuring directly power output, segments with steep downhills must be excluded
   Data segments with non-comparable environmental conditions such as running in soft sand or in head-wind or tail-wind can be excluded if correction factors are not used in calculation.
6) Selecting most reliable data segments for further analysis; or selecting all data segments for further analysis wherein data segments with high reliability have high weighting coefficients.
7) Forming an estimate of person's fitness level by utilizing either linear or nonlinear dependency between one or more heart beat derivable parameters and person's performance data or by utilizing performance data only.
8) Giving the person a training plan that is optimal considering his/her fitness level.
9) Utilizing information on user's fitness in automatic guidance of a single exercise session wherein the purpose of automatic guidance is to make the user reach a preset physiological target. Preset physiological target can be set by the user or by an automatic training planning system.

Free fitness test application can be integrated in many devices including e.g. heart rate monitors, mobile phones, PDA devices (e.g. Palm PC) and personal computers, where suitable device has a processor, memory and software stored therein as well as an user interface. The system may have device and a link to external device like heart rate monitor.

The system for implementing the method comprises
   means for inputting personal parameter and exercise type, e.g. user interface having keyboard,
   means for collecting and storing heart beat data during at least one exercise session, e.g heart rate belt and monitor,
   means for collection and storing performance data of each exercise session, e.g. a bicycle ergometer, means for segmenting collected data to different heart rate ranges, means for calculating the reliability of each data segment, means for calculating weighting coefficients for each data segment based on calculated reliability, means for calculating an estimate of user's fitness level based on dependency between the heart beat data segments and said performance data using the calculated weighting coefficients.

In certain conditions there is a shortcut to evaluate a minimum fitness level. Said collected performance data is analyzed to find the minimum possible value of user's fitness and an estimate of user's cardiorespiratory fitness level is formed based on the analyzed minimum possible value only instead using data segments and the calculated weighting coefficients.

The analyzing, segmenting and calculation are performed by software stored in the device. A blood lactate analyzer may be used to measure blood lactate level. An air flow meter may be used to measure respiration rate or ventilation.

After setting personal parameters and selection of exercise type (e.g. walking or pole (nordic) walking or running outdoors/on a treadmill; cycling outdoors/on a bicycle ergometer; ergometer rowing) user starts to exercise. In addition to the exercise types listed above, numerous other exercises can be used since there are equations for calculating theoretical oxygen consumption (theoretical VO2) for many other exercises as well. Calculation is based on either positional/altitude data or power output measurement. User can freely change the intensity of exercise. Collection of heart beat data during exercise can be done using equipment of current state of art. Simplest way is to use heart rate transmitter belt and recording of transmitted data to a receiver/recorder unit. Also a heart beat recording belt can be utilized for the purpose. Free fitness test can be applied in many exercise disciplines. Possible exercise disciplines include: (Pole)Walking/running and cycling outdoors, bicycle ergometer, rowing ergometer, Walking/running on a treadmill. In the described invention cardiorespiratory fitness assessment is based on measurement of speed and altitude (or inclination of a treadmill), or power production of the testee which can be derived when performing previously described exercise disciplines. Possible combinations for the assessment of oxygen consumption are: accelorometry+altimetry, GPS or Galileo (or other satellite navigation system) based positioning (+altimetry), measurement of treadmill speed+inclination and measurement of external power. It is also possible to utilize local (indoor) positioning in the assessment of theoretical oxygen consumption by taking available techniques in use, such as techniques that are based on Wi-Fi/WLAN positioning or other similar technique such as Bluetooth, Radio Frequency Identification (RFID) technology, ultrasound, Ultra Wide Band (UWB) technology, optical positioning or TV radio signals (see e.g. Ekahau RTLS system, CA, USA and http://www.indoorlbs.com/id115.html). During outdoor cycling power may be measured using either combination of crank torque and cadence or chain vibration and cadence or other similar method, or by calculating the power by utilizing different equations for mechanical work (see e.g. Martin et al 1998). In stationary bicycles workload (i.e. how much the flywheel is broken) is adjusted usually by magnetic or electromagnetic means or by utilizing friction. In rowing workload/resistance is usually adjusted by magnetic means, or using air or friction resistance. In exercise machines workload information can be either sent or input to a calculation unit (central processing unit, CPU) or calculated in the exercise machine itself. Data can be sent wirelessly by means of e.g. infrared, bluetooth or other similar method; or by using a wired connection. Wireless communication between an exercise machine and a PDA device has been described in patent application publication EP1527801: In the document a universal, exercise machine mounted PDA holder is disclosed. When placed to the universal holder different kinds of PDA devices communicate with an exercise machine through an infrared signal. Of course, it is possible to attach external measurement devices to fitness machines too. External measurement devices can comprise a separate CPU/display unit to which data can be sent wirelessly or by using wired connection which has been described e.g. in US2002/0160883 (Dugan) and in U.S. Pat. No. 7,030,735 (Chen).

As the first step of analysis, external workload is calculated in long sliding windows, say 3 min windows, to calculate the lowest possible value of person's fitness. Generally data segments have each duration of 20 s-10 min, preferably 30 s-4 min. Estimate of minimum level of person's fitness can be made since it is not possible to maintain any external workload harder than the level of maximal oxygen consumption for longer than a few minutes. Minimum level of person's fitness is calculated by calculating the value of oxygen consumption value corresponding to the external workload by using an appropriate equation (equations are presented later in this document).

After the minimum possible value of person's fitness is estimated data is segmented, each segment representing a given heart rate range. Ranges can be e.g. 100-109, 110-119 . . . 190-199, or the ranges can base on % HRmax (51-55%, 56-60% . . . 96-100%). In one embodiment only one data segment with preset criteria is selected to present a given range but there can also be several data segments, or their average presenting each range. Selected data segment is thought to most accurately reflect person's fitness.

Data segments with low reliability can be excluded from further analysis. Firstly data segments with significant decreases in heart rate are excluded. Secondly, every time when power output is not directly measured (i.e. when power output is derived from speed and altitude/inclination data), data segments comprising too steep downhill are excluded from further analysis. This is also done in cycling if workload is calculated based on speed, altitude and wind. Thirdly, data segments with measured or reported non-comparable environmental conditions can be excluded in cases when no correction factors are used. As an example, e.g. segments with excessive head-wind or tailwind can be excluded from further analysis if wind speed is measured in proportion to speed of motion. Also data segments with too soft surface can be excluded in the case if running stride is evaluated in more detail and exceptional striding pattern is detected from data. One possible way to recognize different surfaces is to use GPS-positioning and make conclusions based on whether the user is running on a road or in cross-country. It is also possible to include all data segments to further analysis but in this case data segments must be weighted based on their reliability. Data segment with high reliability would have a high weighting coefficient.

Of course, if no correction factors are used, user must be informed before exercise about the factors influencing results. E.g. in the case of running user must be prompted to perform the exercise on a surface which is relatively hard (e.g. running in deep snow or soft sand—or other environment which does not allow normal running technique—does not provide accurate results.). Actually, every time when fitness determination (estimation of person's VO2max or METmax) is made based on information on speed, user must be informed on the effect of different surfaces to the estimation accuracy. As a second example, also cycling speed is influenced by the surface: (gravel/sand/mud vs. asphalt).

After weighting data segments based on their reliability or alternatively—excluding low reliability data segments and selecting the best data segments for final analysis —final analysis of fitness is made utilizing either linear or non-linear dependencies between heart beat derived parameters and performance parameters; or by selecting the above described minimum possible value of person's fitness if only it gives higher estimate than linear or non-linear equations. If a single exercise session does not include enough reliable data, data from several exercise sessions can be utilized.

Information on person's fitness can be utilized both in automatic guidance of single exercise and in automatic planning of future training.

DESCRIPTION OF THE DRAWINGS

The invention and its embodiments are described more in detail with reference to following drawings.

DETAILED DESCRIPTION OF INVENTION

Figure 1:
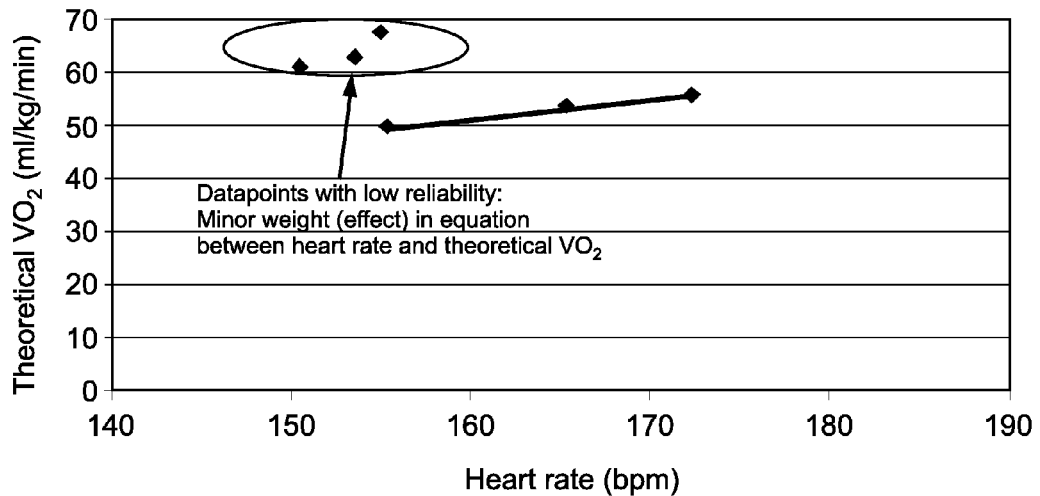
FIG. 1 presents measured points in recorded heart beat data and selection of points to be used

In one embodiment of described invention fitness estimate is provided each time when the user has measured required parameters (HR+speed and altitude/inclination or HR+power production). User is equipped with heart rate monitor (or similar device), and a speed and altitude or a power measuring device. Before beginning the test user sets background parameters: A) If the user is using a software or device equipped with fitness test for the first time, the user is prompted for setting required background parameters automatically (age or preferably HRmax; gender; weight is required e.g. in ergometer cycling and ergometer rowing). B) Otherwise user may adjust the previously set background parameters from the settings menu and setting parameters is thus not mandatory. User starts exercise: Walking/jogging, (bicycling or rowing). If real-time monitoring is desired, user may observe estimated fitness level throughout the test. Reliability of the fitness estimate is also provided (e.g. scale 0-100%). User observes the final fitness estimate after the test. VO2max estimate of a single exercise session can be displayed to the user if there are enough reliable and physiologically meaningful data points during the exercise session.

In one embodiment of described invention the progress of the user's cardiorespiratory fitness is evaluated. User has performed a plurality of exercise sessions equipped with appropriate equipment. After the exercise the user may browse his/her progress in a form of a graph or numbers. A feedback can be provided to the user about his progress. Progress information can be also utilized to provide the user more suitable training plans for the future.

In one embodiment of described invention user's cardiorespiratory fitness is evaluated during a training session where user's intensity during the training session is automatically guided by an intensity guidance method (patent applications US2006/004265 (FI-U-6796) and WO2008/003830 by Firstbeat Technologies). User selects a route or distance to cover and a physiological target state (e.g. Training Effect or EPOC target) for the exercise. Either one or both of route/distance and physiological target state can be also prompted by the system. The location of start and end of route is preferably the same which allows the user to shorten his exercise if needed. User starts to exercise. During the workout pre-predicted fitness level estimate gets more accurate which is used to enhance the intensity guidance. By enhancing the intensity guidance preset targets can be reached more precisely. When available training time has run out the user should preferably have covered preselected route and reached his/her target EPOC/TE. It is also possible to change preset route if system estimates the session to become too hard for the user: user will not be able to cover the whole preselected route but will still reach target TE/EPOC when arriving to the end point of route.

In one embodiment one or more of the heart rate and performance parameters are input manually by the user during the exercise.

In one embodiment of described invention it is possible to give to user instructions before and/or during the exercise on how to get as accurate results as possible. During the exercise these prompts may include messages such as "go faster" or "go slower" so that the system gets appropriate amount of data at different intensities.

In one embodiment of described invention given heart rate ranges are detected from the heart beat time series. Heart rate ranges may be e.g. 120-129, 130-139 . . . 190-199. Taking into account the principles of exercise physiology and fitness testing, best possible parts of heart beat time series are selected to represent above mentioned ranges. Generally, the quality of data is the better the longer the series of successive heart beat intervals is and the smaller is the variation in heart rate level. E.g. If taking data to represent heart beat range 150-160 bpm, there can be several segments of data which could be taken to represent this heart rate range. However the data segment with highest reliability (long duration and low variability) is taken to represent this range. The reliability can be evaluated e.g. as shown below in table 1:

TABLE 1

| Standard deviation of successive 10 sec heart rate values (beats per minute) | Duration (min) | | | | | |
|---|---|---|---|---|---|---|
| | less than 0.5 min | 0.5-1.0 min | 1.0-1.5 min | 1.5-2.0 min | 2.0-2.5 min | 2.5-3.0 min |
| | Reliability coefficient (%) | | | | | |
| more than 3.0 bpm | 3% | 6% | 8% | 11% | 14% | 17% |
| 2.5-3.0 bpm | 6% | 11% | 17% | 22% | 28% | 33% |
| 2.0-2.5 bpm | 8% | 17% | 25% | 33% | 42% | 50% |
| 1.5-2.0 bpm | 11% | 22% | 33% | 44% | 56% | 67% |
| 1.0-1.5 bpm | 14% | 28% | 42% | 56% | 69% | 83% |
| less than 1 bpm | 17% | 33% | 50% | 67% | 83% | 10% |

Of course, the data could be also segmented to different ranges of theoretical oxygen consumption (theoretical VO2), e.g. 10-15, 15-20 . . . 50-55 ml/kg/min, or to ranges of % of maximal heart rate (% HRmax), e.g. 51-55%, 56-60%, 61-65% . . . 96-100%.

Naturally, there could be several selection surfaces where the criteria change slightly depending on heart rate ranges. In higher heart rate ranges the variability of heart rate during a given external work is found to be lower than at lower heart rate levels. Accordingly, variability limits could be stricter at higher heart rate levels.

In one embodiment it is possible to include all data segments to further analysis. In this embodiment each data segment is weighted based on their reliability. In this case data with high reliability has also a high weighting coefficient when forming the linear/non-linear equations between external power output (theoretical oxygen consumption) and physiological exercise parameters (See FIG. 1.).

Also the requirements for the length of data segment could be slightly different at different heart rate levels to enhance discriminating power between different data segments.

There should be a relatively wide range of heart rate levels in use to ensure sufficient accuracy for the fitness (e.g. VO2max) determination. In one embodiment of described invention, if available heart rate level range is determined to be too narrow, it would be widened by preferring lower end and higher end data segments. In the described embodiment segments with greatest heart rate averages are preferred within segments of highest heart rate range (see table 2): reliability percentages from tables 1 and 2 are multiplied together and the segment with highest product is selected. Similarly, smallest values of lowest heart rate range are preferred (see table 3). Then reliability percentages from table 1 and 3 are multiplied together and the segment with highest product is selected. E.g. If highest available heart rate range is 150-160, then a data segment with average heart rate of 159 could be preferred over a data segment with average heart rate of 152 although the length of latter data segment would be slightly higher and variability slightly lower than in former data segment. Of course, if the quality of the data segment with higher average heart rate would be too low, then the data segment with lower heart rate would be selected to VO2max determination. Similarly, if there was a need to extend intensity range at the lower end, e.g. a data segment with average heart rate of 122 could be preferred over a data segment with average heart rate of 127 if only the length and reliability of the former segment were sufficient.

TABLE 2

| Average heart rate of segment when 150-159 is the highest available heart rate range | Reliability coefficient |
|---|---|
| 150-151 | 60% |
| 152-153 | 70% |
| 154-155 | 80% |
| 156-157 | 90% |
| 158-159 | 100% |

According to table 2, in a case that heart rate range 150-159 is the highest available heart rate range for a person; if e.g. the reliability of a data segment (based on length and data variation) with average heart rate of 158 beats per minute would be 33%, then the total reliability would be 33%*100%=33%. A more reliable segment (reliability %=50% based on based on data length and variation) with average heart rate of 151 would produce a total reliability of 50%*60%=30%. This would mean that the former data segment with average heart rate of 158 would be selected to further analysis.

TABLE 3

| Average heart rate of segment when 120-129 is the lowest available heart rate range | Reliability coefficient |
|---|---|
| 120-121 | 100% |
| 122-123 | 90% |
| 124-125 | 80% |
| 126-127 | 70% |
| 128-129 | 60% |

According to table 3, in a case that heart rate range 120-129 is the lowest available heart rate range for a person; if e.g. the reliability of a data segment (based on length and data variation) with average heart rate of 120 beats per minute would be 33%, then the total reliability would be 33%*100%=33%. A more reliable segment (reliability %=50% based on based on data length and variation) with average heart rate of 129 would produce a total reliability of 50%*60%=30%. This would mean that the former data segment with average heart rate of 120 would be selected to further analysis.

Of course there are numerous other possible heuristics for determining the reliability of data. Another simplified example is below in table 4. Of course it is possible to use e.g. neural network in determining the reliability of data segments.

TABLE 4

| A) SD of successive 10 sec heart rates is less than 2 bpm | B) Average heart rate of previous segment differs less than 10 bpm | C) Duration at least 1.5 min | Reliability |
|---|---|---|---|
| X | | | 33.3% |
| | X | | 33.3% |
| | | X | 33.3% |
| X | X | | 66.6% |
| X | | X | 66.6% |
| | X | X | 66.6% |
| X | X | X | 100% |

In one embodiment of described invention, if external workload increases during a data segment, average external work load (theoretical oxygen consumption) and highest 15 sec average of heart rate used to form the equation based on which person's fitness is evaluated. On the contrary, if external workload decreases during a data segment, average external workload and lowest 15 sec average heart rate are used to form the equation based on which person's fitness is evaluated. Almost similar solution would be selecting average external workload and average heart rate of 15 last seconds in all data segment. These solutions should most accurately correspond steady state conditions.

FIG. 2 shows a typical freely performed exercise session which has been performed by running. There is data segment in the beginning of exercise (dark grey segments) which has highest 3 min average theoretical VO2. This segment with average theoretical VO2 of 55 ml/kg/min is considered as the minimum possible VO2max of the testee. After determining the minimum value of person's VO2max data is segmented and appropriate data segments (light grey segments) are selected from the whole exercise session. For clarity only 5 data segments are introduced in this example (see table 5). Data is segmented into segments with similar heart rate level. Data segments with low variance (measured by e.g. variance or standard deviance) and long duration are preferred for further analysis. The reliability of a data segment is assumed to be better if previous data segments have similar external workload. Segments 3, 4 and 5 (see table 5) are determined to best suit for fitness determination.

TABLE 5

| Segment no. | HR | Theoretical VO2 (ml/kg/min) | Reliability (%) | Notes |
|---|---|---|---|---|
| 1 | 172 | 67 | 22% | Included to further analysis |
| 2 | 141 | 36 | 30% | Included to further analysis |
| 3 | 156 | 44 | 69% | Included to further analysis |
| 4 | 145 | 47 | 14% | Excluded from further analysis |
| 5 | 168 | 55 | 28% | Included to further analysis |

Figure 3:
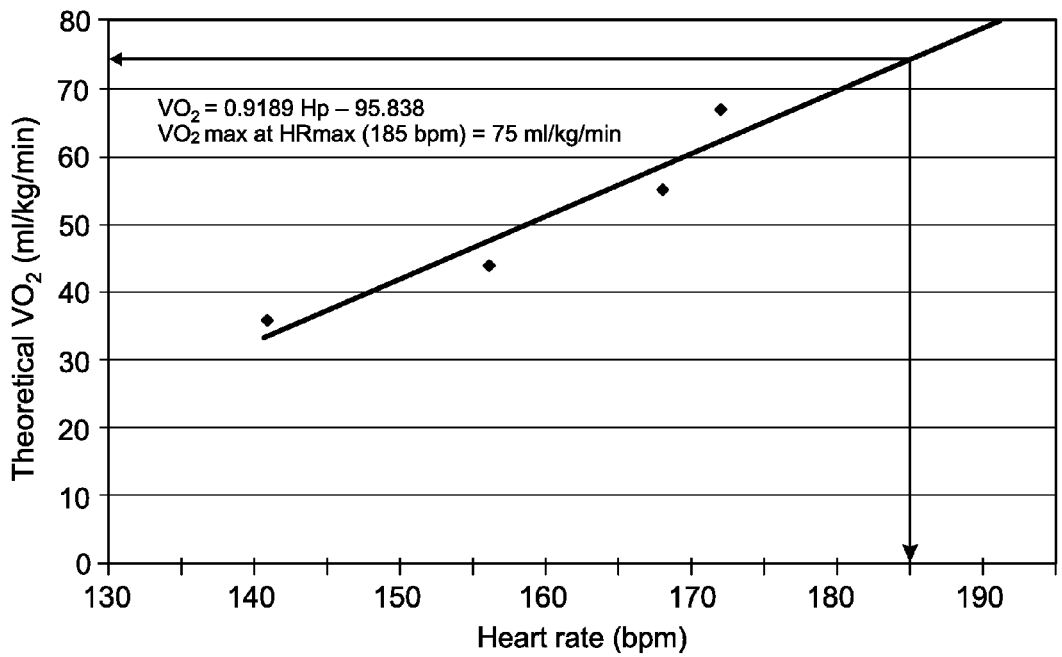
FIG. 3 presents a linear equation of the chosen segments to estimate fitness
Figure 2A:
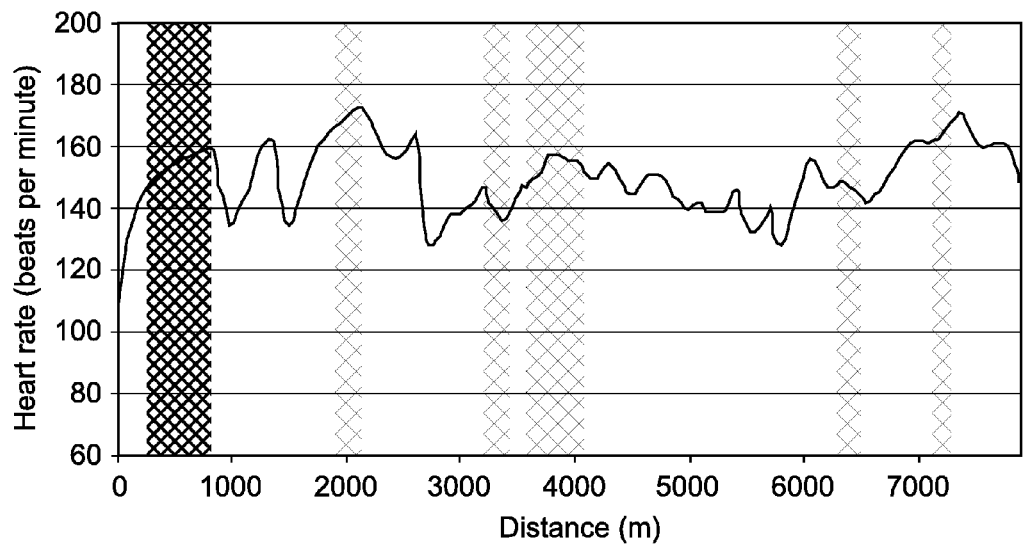
FIGS. 2*a*-2*d* present for parameters in recorded data of freely performed exercise session by running and showing segments with defined reliability
Figure 2B:
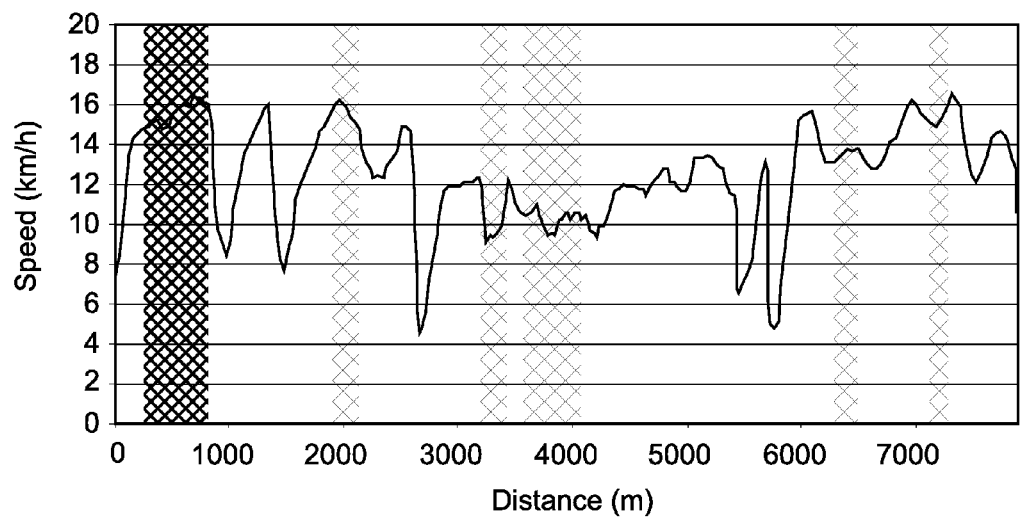
Figure 2C:
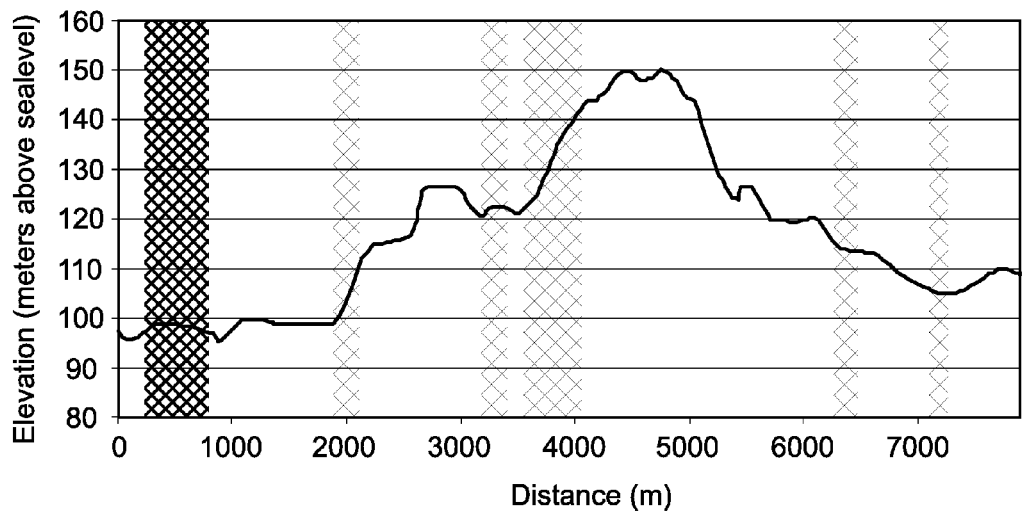
Figure 2D:
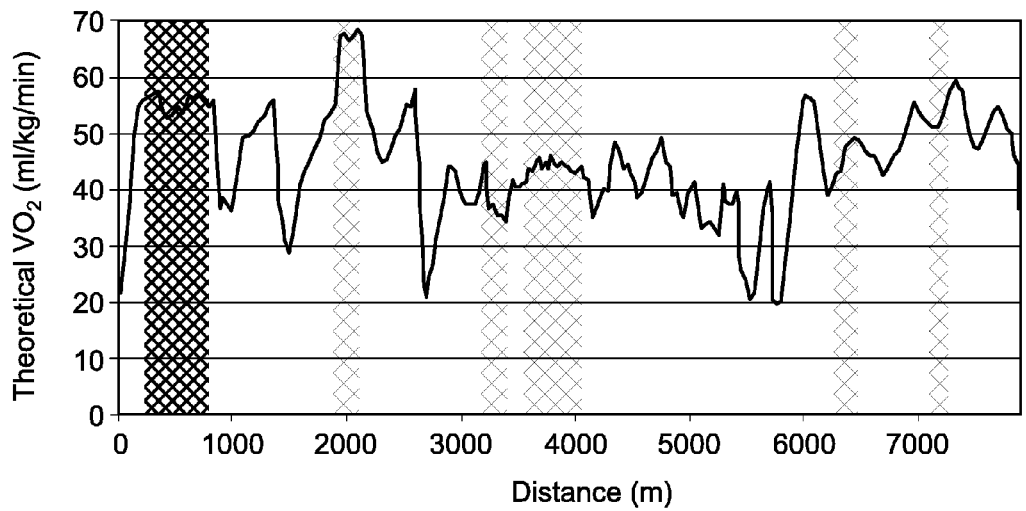

Linear equation is made from segments 1, 2, 3 and 5, and the linear equation results in a VO2max of 75 ml/kg/min (person's maximal heart rate is 185) (see FIG. 3.).

As a good example, data segment 4 (in table 5) is analyzed in more detail. Data segment was excluded due to it's low reliability as compared to segment 2 (both segments represent same heart rate range 140-149). The low reliability of segment 4 is due to its short duration and highly increasing intensity.

In one embodiment of described invention the reliability of position/altitude/speed data is evaluated. It is possible to filter speed signal or to detect and exclude from further analysis the moments when GPS-signal is too weak.

In one embodiment of described invention it is possible to predict the type of activity (running or walking) based on person's speed or limb acceleration data, and use appropriate VO2 calculation formula which best suits for the activity. When prediction is used, the user must not define the type of exercise before exercise. When distinguishing the type of activity between walking and running, moments with speed lower than 7 km/h could be defined as walking and moments with speed equal to or higher than 7 km/h could be defined as running.

In one embodiment of described invention the equations for calculating theoretical oxygen consumption from external workload are the following:

Walking and Pole Walking:

$$\text{Theoretical VO2 (ml/kg/min)} = 1.78 * \text{speed} * 16.67 * [\tan(\text{inclination}) + 0.073]$$

Running on a Level Ground:

$$\text{Theoretical VO2 (ml/kg/min)} = 3.5 * \text{speed}$$

Running in a Hilly Terrain:

$$\text{Theoretical VO2 (ml/kg/min)} = 3.33 * \text{speed} + 15 * \tan(\text{inclination}) * \text{speed} + 3.5$$

Cycling:

$$\text{Theoretical VO2 (ml/kg/min)} = (12.35 * \text{Power} + 300) / \text{person's weight}$$

$$\text{(Indoor) rowing VO2 (ml/kg/min)} = (14.72 * \text{Power} + 250.39) / \text{person's weight}$$

Unit of speed=kilometers per hour (km/h)
Unit of inclination=degrees)(°)
Unit of power=watts (W)
Unit of weight=kilograms (kg)

The above presented equations are well-known from the prior art.

In addition: equations has been described by Martin et al. (1998) for the calculation of road cycling power based on measured speed and altitude data etc. based on which VO2 can be calculated. It is however irrelevant to show these equations in here.

Figure 4:
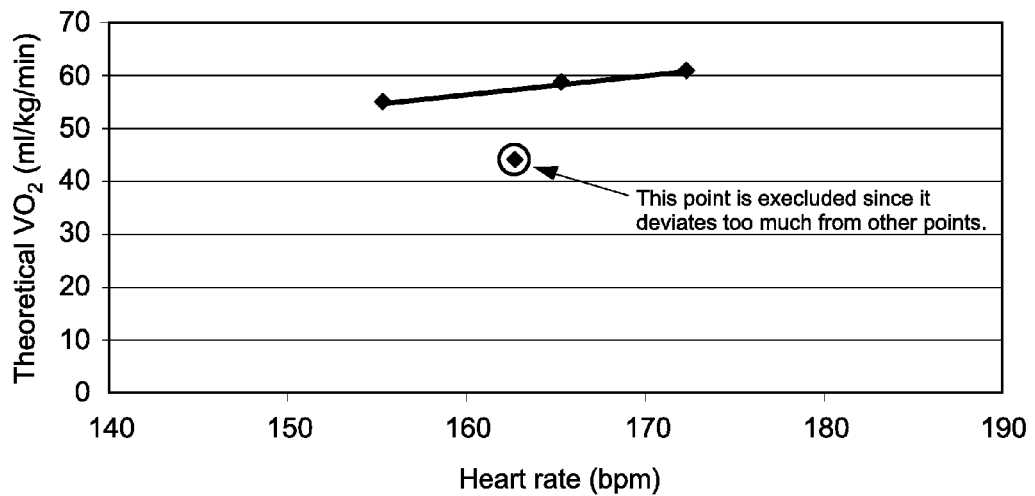
FIG. 4 presents excluding a data point with excessive deviation

In one embodiment of described invention data points with excessive deviation from other data points are also excluded from fitness determination. (See FIG. 4, where bpm=beats per minute).

In one embodiment of described invention changes in exercise intensity are evaluated based on heart beat derivable EPOC (Excess post-exercise oxygen consumption). The derivation of EPOC from heart beat data is described in U.S. Pat. No. 7,192,401 (Patent by Firstbeat Technologies).

In one embodiment of described invention the data points for fitness determination are selected from two or more exercise sessions. This is done especially if one exercise session does not provide enough reliable data for fitness determination. The accuracy of fitness estimate is better than when data from several exercise sessions are used as compared to estimation based on one exercise session only. "Estimation error caused for example by environmental factors (wind, road surface etc) can be minimized or even excluded with data or fitness level estimates from several exercise sessions. This is in especial advantage in PC or in web software application which can utilize easily massive amount of data In one embodiment of described invention one or more parameters other than heart rate and external workload are used in fitness determination. These additional parameters can be heart beat derivable parameters. Possible parameters include respiration rate and ventilation (U.S. Pat. No. 7,460, 901 by Firstbeat Technologies Oy), blood lactate, subjective feelings (e.g. Rating of perceived exertion, RPE), heart rate variability (HRV) or other similar parameter.

Figure 6:
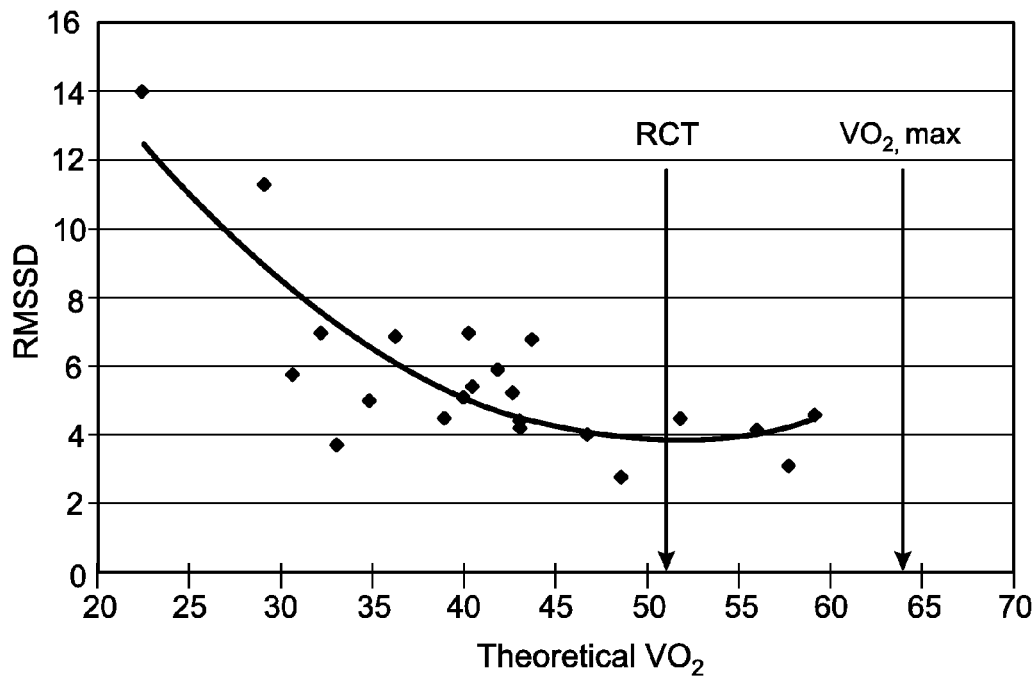
FIGS. 6 and 7 present determining of VO2 Max, or HRMAX respectively, using threshold values heart rate variability or respiration
Figure 7:
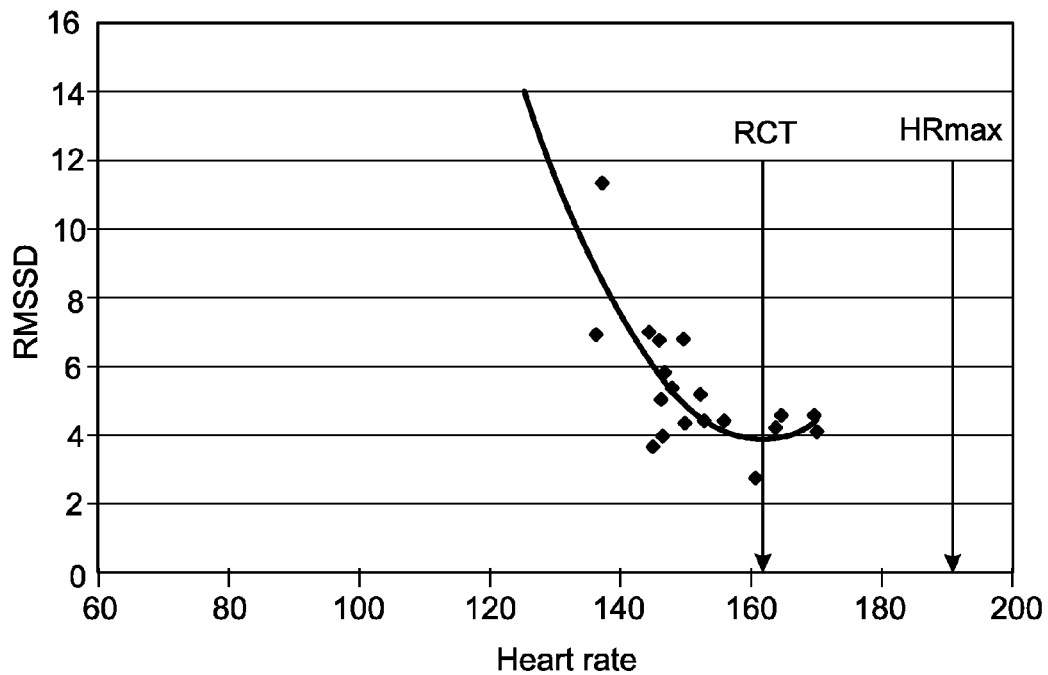

Use of HRV in the determination of maximal heart rate and fitness have been recently described by Lewis et al. (2007), Oshima & Shiga (U.S. Pat. No. 7,326,150), Shiga et al (EP1059102), Heikkilä (U.S. Pat. No. 5,810,722 and Heikkilä & Pietilä (EP0748185) but not during free exercise sessions which require data segmentation and evaluation. In one embodiment of described invention external workload is monitored against heart rate variability. In the described embodiment data is first segmented as described elsewhere in this document. One or more heart rate variability indices are calculated for reliable data segments. Of course, it is possible to select all data segments in which case segments are weighted based on their reliability. HRV data can be utilized in two different ways: either to increase the accuracy of estimating person's HRmax which information is further utilized in fitness determination; or to directly estimate person's cardiorespiratory fitness (VO2max) based on heart rate variability information. Person's cardiorespiratory fitness can be evaluated by utilizing either linear or non-linear mathematical equations between any given HRV index and external workload or theoretical VO2 (For the use of HRV information in estimation of cardiorespiratory fitness, see the FIGS. 6 and 7, where RMSSD [Root Mean Square of Successive Differences in RR Intervals] is used as the HRV index, and theoretical VO2 is measured as ml/kg/min and heart rate (HR) as beats per minute). In one embodiment increasing the estimation accuracy of person's HRmax can be performed in a way that the equation—HRmax=210−0.65*age—is used but this value is slightly up- or downgraded depending on the HRV response during exercise. Of course, it is possible to estimate person's HRmax based on person's exercise induced HRV response only. Minimum value of HRV is usually reached at about 75-85% of HRmax (respiratory compensation threshold, RCT), and therefore HRmax≈HR_at_RCT/0.80. Similarly when RCT is expressed as % VO2max it is usually reached at about 70-80% VO2max and therefore VO2max≈VO2_at_RCT/0.75.

Figure 8:
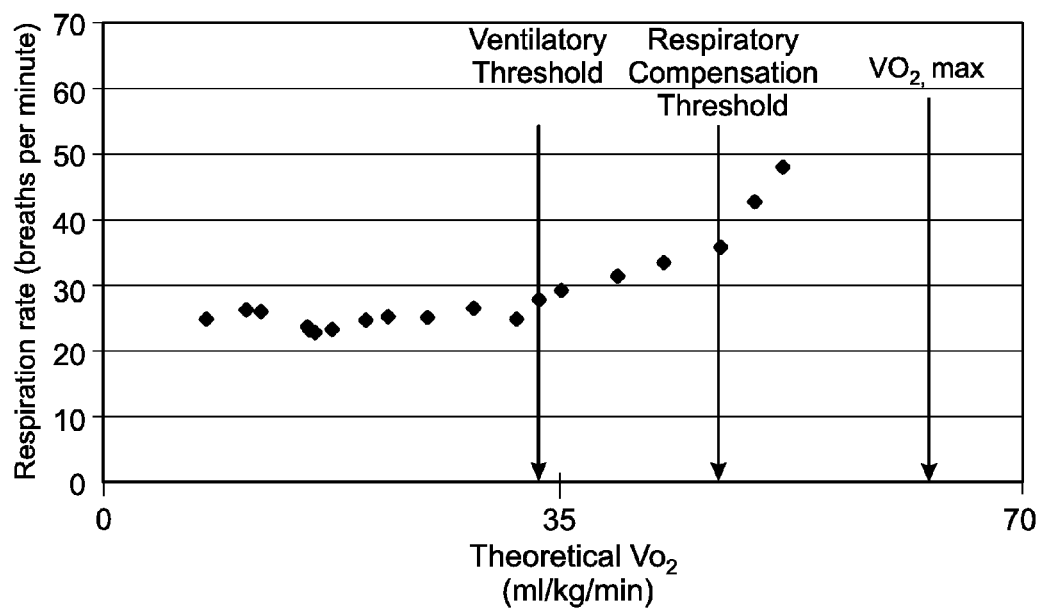
FIG. 8 presents a similar graph as FIG. 6 using respiration rate instead of RMSSD

In one embodiment of described invention external workload is monitored against RPE-values reported by the user during the exercise (see FIG. 8). Data segments with excessive variation in external workload are excluded from further analysis. This is done because the dependency between user's rating of perceived exertion and external workload is distorted when external workload fluctuates. RPE scale starts from 6 (perceived exertion equivalent to doing nothing) and ends to 20 (perceived exertion equivalent to exhaustion). The described embodiment can be implemented in e.g. in a mobile phone where the user types his RPE values. In described embodiment the system can ask the user to report current RPE.

Figure 5:
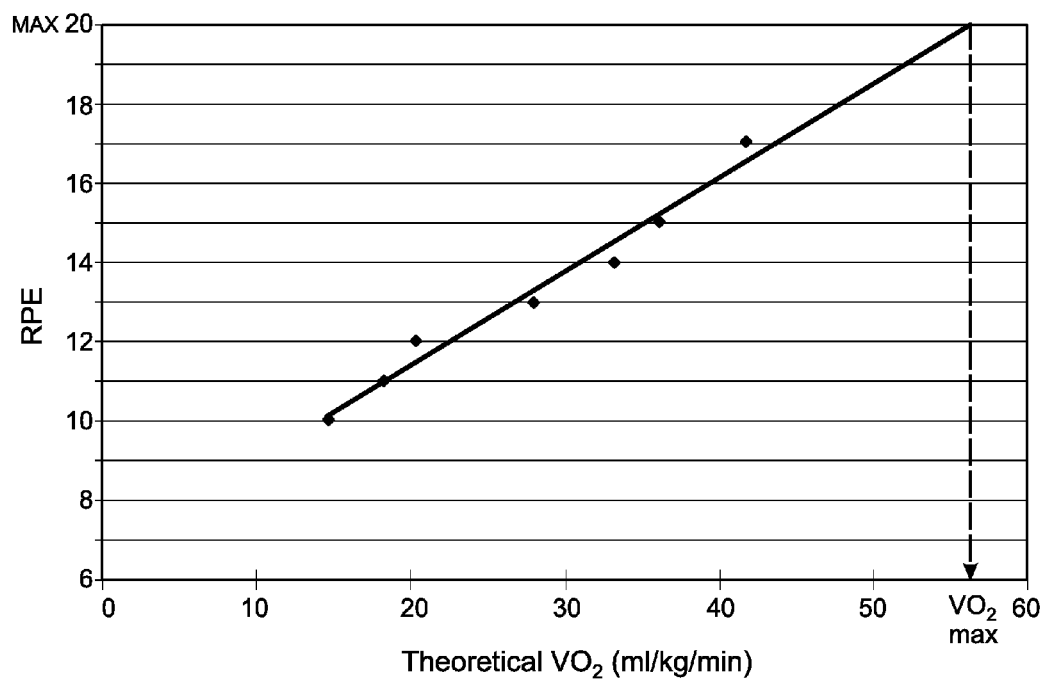
FIG. 5 presents estimation fitness based on rating of perceived exertion (RPE)

Borgs RPE-scale 6
7-Very, very light
8
9-Very light
10
11-Fairly light
12
13-Moderately hard
14
15-Hard
16
17-Very hard
18
19-Very, very hard
20-Exhaustion In one embodiment of described invention external workload is monitored against respiration rate (see FIG. 5) or ventilation wherein both respiration rate and ventilation can be derived from HRV as described in U.S. Pat. No. 7,460,901 by Firstbeat Technologies (Saalasti & Kettunen). In the described embodiment one or more metabolic thresholds are determined based on changes in respiration rate and ventilation, and VO2max is determined based on information on said metabolic thresholds. E.g. ventilatory threshold is determined as the first and RCT is determined as the second non-linear increase in respiration rate or ventilation as a function of theoretical VO2 or power output. In this case VO2max=VO2 at RCT /0.75 or VO2max=VO2 at ventilatory threshold/0.50.

In one embodiment of described invention fitness determination is done based on recovery characteristics of heart rate or heart rate variability after free user performed exercise session. In this embodiment external workload is measured during the exercise. Fitness is evaluated using a databank containing a large amount of exercise and related recovery data. Neural network modeling can be utilized in a way that a neural network is taught with large amount of exercise and recovery data.

In one embodiment of described invention fitness determination is done using a neural network.

In one embodiment of described invention reliability percentage of the fitness estimate is shown to the user e.g. as "goodness of fit" ($r^2$)-value.

In one embodiment of described invention fitness determination is done utilizing one or more methods described in this document. Person's VO2max can be calculated e.g. as a mean or weighted mean of several calculation methods or by utilizing a neural network model.

Following example of software shows a Matlab® m-function, which is used to estimate VO2max based on ambulatory recordings of heart rate, speed and altitude. This particular function suits for analysis of data that have been recorded with Suunto® T6 wristop computers. As is obvious to a person skilled in art, by slightly modifying the matlab m-function it could be used with other file types as well, e.g. file types wherein only heart rate, position and altitude are provided.

In this example, the data is handled in 4 minute sliding window. Each sliding window is evaluated with parameters heart rate (bpm) and speed (m/s). Accepted variation in heart rate is 2.5 bpm and in speed 1 m/s. Data segment is formed, when 85% of the sliding window falls into this criteria. In this example, 85% represents the reliability. Then weighting coefficient values are 1 and 0 according to this rule.

Alternatively, instead of fixed 85% reliability threshold, weighing coefficient value can be calculated for each data segment to be continuously between 0-1 according to a function using percentage value as a variable. The percentage value is the proportion of whole data segment duration and the accepted length with chosen criteria (see c1 and c2 in example 1). Data was segmented in this example by using characteristics of the data itself. This means usually searching coherent (usually steady) periods in each parameter (typically intensity and performance data like speed) in respect to its level and variation.

Data segment can be accepted with more complex rules comprising other parameters than those concerning intensity and performance data, for example related to data segment duration.

Additional criteria for reliability can be formed by evaluating the maximum intensity reached during the exercise. For example the whole result can be rejected if the maximum intensity has not reached a certain threshold, for example 40% maximum intensity.

```
% Matlab ® m-function to estimate VO2max based on ambulatory recording with
% Suunto T6 ®. T6-sdf file containing [POINTS] is stored in a
% matrix-form to a matlab-structure S. Sampling frequency of
% POINTS-matrix is 10 seconds (rows are time series). Also [HEADER] of the
% sdf-file is used.
%
% Algorithm in short: each datapoint is checked if its surrounding, defined
% with a window of length n, meets the variance limits defined by
% coefficients c1 and c2. Only those datapoints accepted are used in the
% linear regression fit VO2teor=b(1)*HR+b(2). VO2max=b(1)*HRmax+b(2).
% VO2theor is estimated using speed and running angle.
%
% Inputs
%      c1      How much heart rate (bpm) may vary
%      c2      How much speed (m/s) may vary
```

```
%      n           The size of the window in which the time series are calculated.
%      p           How many percent the window must contain data restricted by
%                  c1 and c2 to be accepted.
%
% Outputs
%      VO2max      VO2max estimate in ml/kg/min
%      b           The coefficients of the linear regression
%      ind         Indices of the time series that were accepted for linear
regression
%      HR          Heart rate of the time series
%      VO2theor Theoretical running VO2 ml/kg/min based on speed and running
angle.
%
% Example:
% Inputs
%      c1          heart rate (bpm) may vary 2.5 bpm
%      c2          speed (m/s) may vary 1m/s
%      n           time window 4 minutes periods
%      p           85% needs to be within criteria c1 and c2 in the time set
%                  window n (4 minutes).
% [VO2max, b, stats, ind, HR, VO2theor]=vo2_5(s,2.5,1,6*4,0.85);
% plot(HR,VO2theor,'.');
% hold on;
% plot(HR(ind),VO2theor(ind),'r*');
% plot(HR,polyval(b,HR))
% title(['Estimated VO2max=' num2str(VO2max)]);
% xlabel('HeartRate (bpm)'); ylabel('VO2theor ml/kg/min');
% hold off;
%
function [VO2max,b,stats,ind, HR, VO2theor] =vo2_5(S,c1,c2,n,p);
v=S.POINTS(:,14);
alti=S.POINTS(:,2);
dist=S.POINTS(:,13);
HR=S.POINTS(:,5);
altiD=zeros(length(alti),1).*0.001; altiD(2:end)=alti(2:end)-alti(1:end-1);
distD=zeros(length(dist),1).*0.001; distD(2:end)=dist(2:end)-dist(1:end-1);
VO2theor=12.*v+54.*tan( (sin(altiD./distD).*pi./180) ).*v+2.5;
HRmax=str2num( S. HEADER( strmatch('PERSONAL_MAXHR',S.HEADER) ,16:18) );
% HR and VO2theor must be nanfree. Heart rate should be at least 80,
% VO2theor>10 and speed at least 1m/s.
accepted_inds=find(~isnan(HR) & ~isnan(VO2theor) & HR>80 & VO2theor>10 & v>1);
ind=[ ];
n2=round(n/2);
for i=1:length(HR),
    t=intersect(accepted_inds, (i-n2):i+n2);
    if length(t)>=n2 & length(find(HR(t)>=HR(i)-c1 & HR(t)<=HR(i)+c1 &
VO2theor(t)>=VO2theor(i)-c2 & VO2theor(t)<VO2theor(i)+c2))>=p*length(t),
        ind=union(ind,t);
    end;
end;
if length(ind)<10,
    disp('Too few datapoints!');
end;
[b,stats]=polyfit(HR(ind),VO2theor(ind),1);
VO2max=HRmax*b(1)+b(2);
```

The invention claimed is:

1. A method for evaluating cardiorespiratory fitness of a user during an exercise, said evaluating being performed by a device including a processor, memory and software stored therein, and a user interface, the device being one of a heart rate monitor, a mobile phone, a PDA device, a wristop computer, and a personal computer, the method comprising the steps of:

selecting exercise type and inputting user's physiological background parameters using the user interface of said device, during at least one exercise session, continuously collecting heart beat data comprising heart beat time series by an equipment suitable for obtaining heart beat data, and continuously collecting performance data by one of a satellite navigation system (GPS, Galileo), an accelerometer, bicycle ergometer, rowing ergometer, treadmill, and wristop computer, segmenting said collected heart beat data to data segments with coherent intensity by grouping continuous heart beat data having values that are within specified ranges, calculating reliability of the data segments based on a duration and variance of each data segment, and calculating weighting coefficients for the data segments based on their calculated reliability relative to a threshold reliability value, and obtaining an estimate of user's cardiorespiratory fitness level based on a linear relationship between heart rate and a performance output, wherein the heart rate is obtained from the heart beat data segments, the performance output is calculated from the performance data, and the calculated weighting coefficients are used in determining the linear relationship between the heart rate and the performance output.

2. A method as claimed in claim 1, wherein the heart beat data is a heart beat derivable parameter.

3. A method as claimed in claim 1, wherein the heart beat data can be inputted by the user.

4. A method as claimed in claim 1, wherein the heart beat data is rating of perceived exertion.

5. A method as claimed in claim 1, wherein the heart beat data is blood lactate level.

6. A method as claimed in claim 1, wherein the heart beat data is respiration rate.

7. A method as claimed in claim 1, wherein the heart beat data is ventilation.

8. A method as claimed in claim 1, wherein the data segments each have a duration of 20 s-10 min.

\* \* \* \* \*